United States Patent [19]
Hisada

[11] Patent Number: 5,746,731
[45] Date of Patent: May 5, 1998

[54] DISPOSABLE UNDERGARMENT

[75] Inventor: Kenichi Hisada, Ehime-ken, Japan

[73] Assignee: Uni-Charm Corporation, Ehime-ken, Japan

[21] Appl. No.: 632,827

[22] Filed: Apr. 16, 1996

[30] Foreign Application Priority Data

Apr. 26, 1995 [JP] Japan ................... 7-102279

[51] Int. Cl.$^6$ ............... A61F 13/15; A41C 1/00; A41C 1/08
[52] U.S. Cl. ............... 604/385.2; 604/392; 604/396; 450/154; 450/155
[58] Field of Search ............... 604/385.1–402; 2/71–73, 76, 78.3, 109–112, 212–213, 220–222, 400–409, 229, 236, 237, 311, 312, 44; 450/154, 155

[56] References Cited

U.S. PATENT DOCUMENTS

| | | | |
|---|---|---|---|
| 1,410,870 | 3/1922 | Atkinson | 2/78.3 |
| 1,458,082 | 6/1923 | Stein | 2/400 |
| 1,491,528 | 4/1924 | Guinzburg | 2/400 |
| 5,449,353 | 9/1995 | Watanabe et al. | 604/385.2 |

FOREIGN PATENT DOCUMENTS

| | | | |
|---|---|---|---|
| 1104352 | 11/1955 | France | 2/406 |
| 2-33202 | 3/1990 | Japan . | |
| 2-106406 | 8/1990 | Japan . | |
| 3-33201 | 2/1991 | Japan . | |
| 3-82467 | 4/1991 | Japan . | |
| 4289201 | 10/1992 | Japan | 2/401 |

Primary Examiner—John G. Weiss
Assistant Examiner—Karin M. Reichle
Attorney, Agent, or Firm—Lowe, Price, LeBlanc & Becker

[57] ABSTRACT

A disposable belly protector of the present invention includes a front body and a rear body secured together along transversely opposite side edges thereof so as to form a tubular configuration and a pair of first elastic members secured along upper and lower openings of the tubular configuration and a pair of second elastic members secured to at least the front body between the first elastic members so as to extend between the transversely opposite side edges of the front body with a transversely symmetric arrangement which is only curved convexly toward the upper and lower openings, respectively. In another aspect of the present invention, a disposable diaper of pants type is seamlessly connected to the belly protector.

5 Claims, 2 Drawing Sheets

DISPOSABLE UNDERGARMENT

BACKGROUND OF THE INVENTION

The present invention relates to a disposable undergarment such as a belly protector and a combination with such a belly protector.

A belly protector of tubular configuration formed of an elastic sheet material such as a rib stitched fabric is generally known in the art. A belly protector with pants is also known, for example, in Japanese Laid-Open Utility Model Application Nos. Hei2-33202 and Hei2-106406.

However, the known belly protectors have a uniform elasticity and often exert an unacceptable pressure on the wearer's belly particularly when the belly is bulging, sometimes causing an uncomfortably choky feeling for the wearer.

Accordingly, it is a principal object of the invention to provide a disposable undergarment, particularly a belly protector having a pair of elastic members convexly curved, toward upper and lower edges of the belly protector, respectively, to solve the above mentioned problem.

SUMMARY OF THE INVENTION

According to the present invention, there is provided a disposable undergarment comprising a belly protector. The belly protector comprises: a front body and a rear body joined together along transversely opposite side edges thereof so as to form a tubular configuration having upper and lower openings; a pair of first elastic members secured in an elastically contractible condition along the upper and lower openings, respectively; a pair of second elastic members secured in an elastically contractible condition to at least the front body between the pair of first elastic members to extend between the transversely opposite side edges of the front body with a transversely symmetric arrangement and to convexly curve toward the upper, and lower openings, respectively, and one of said pair of second elastic members extending in close proximity of said lower opening.

According to the present invention, there is also provided a disposable undergarment comprising a belly protector and pants. The belly protector is substantially the same as the belly protector mentioned above. The pants comprise: a front body and a rear body joined together along transversely opposite side edges thereof so as to define a waist-opening and a pair of leg-openings; and the waist-opening of the pants being seamlessly connected to the lower opening of the belly protector.

The inventive undergarment, particularly the belly protector integrated with the pants, fits well around the wearer's waist under the effect of the first elastic members. The belly protector, particularly its front body contacts the wearer's belly above and below its prominence under the effect of the second elastic members. In this way, the belly protector fits well around the wearer's waist and belly while a direct pressure exerted on the prominence of the wearer's belly is reliably avoided.

DETAILED DESCRIPTION OF THE PREFERRED EMBODIMENT

Figure 1:
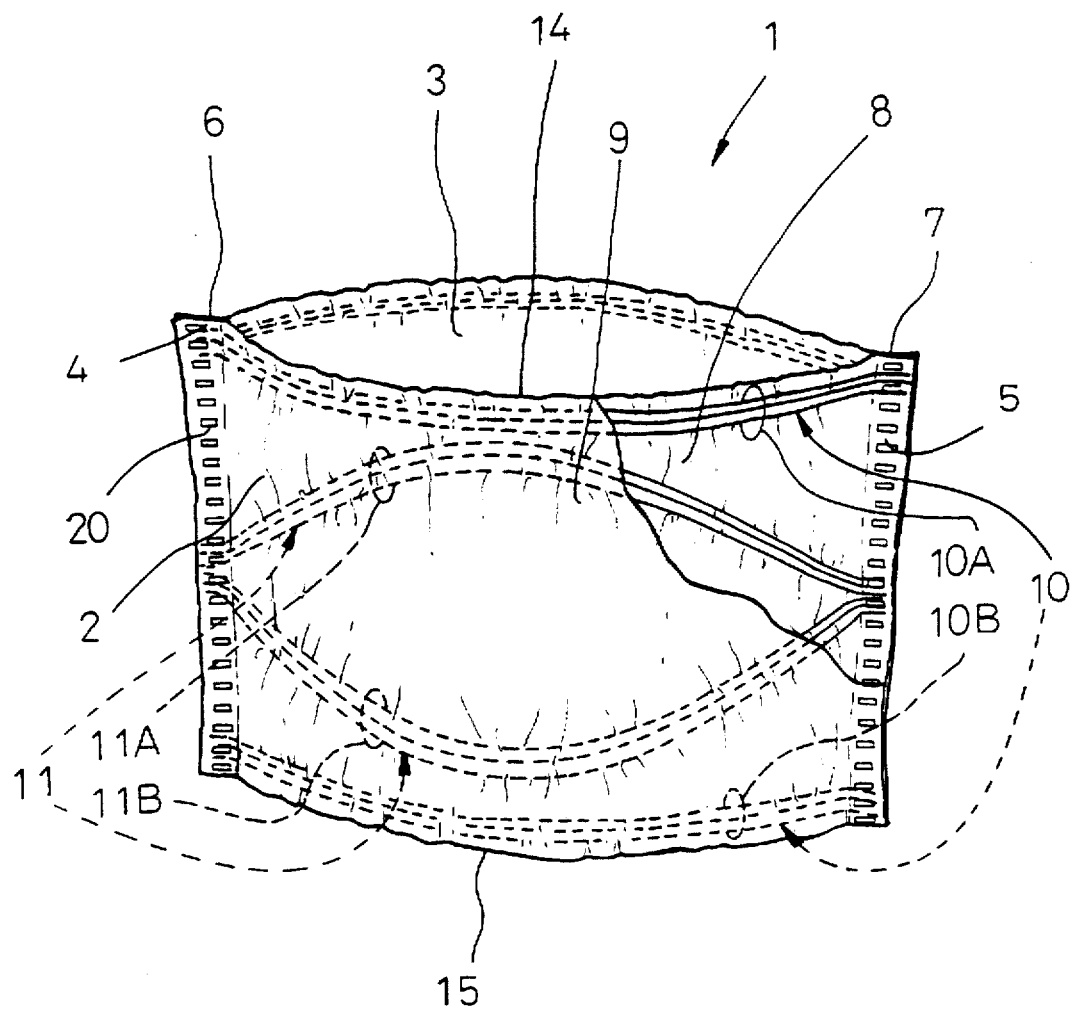
FIG. 1 is a perspective view showing a disposable undergarment as a belly protector of the invention as partially broken away.

Referring to FIG. 1, a belly protector 1 comprises rectangular 2, 3. These front and rear members 2, 3 are joined together along transversely opposite edges 4, 5, 6, 7 in an overlapping relation to form a tubular configuration. Since the front and rear bodies 2, 3 are substantially identical with each other with respect to their constructions, shapes and sizes, these front and rear bodies 2, 3 will be described below only with respect to the front body 2.

The front body 2 comprises inner and outer sheets 8, 9 both formed of a nonwoven fabric containing thermoplastic synthetic fibers of 20 or higher % by weight and first and second elastic members 10, 11 disposed between the inner and outer sheets 8, 9. Each of the first and second elastic members 10, 11 includes a desired number of individual elastic elements. The inner and outer sheets 8, 9 are bonded to each other by heating the thermoplastic synthetic fibers at desired locations or by means of hot melt adhesives applied to the desired locations. The first and second elastic members 10, 11 are secured in an elastically contractible condition to one or both of the inner and outer sheets 8, 9. The first elastic member 10 comprises an upper elastic member 10A extending along an upper opening 14 and a lower elastic member 10B extending along a lower opening 15 of the front body 2. The second elastic member 11 comprises an upper elastic member 11A only curved convexly toward the upper opening 14 and a lower elastic member only curved convexly toward the lower opening 15. The upper and lower elastic members 11A, 11B respectively extend between the side edges 4, 5 with a transversely symmetric arrangement and preferably terminate substantially at middle points of the side edges 4, 5 as viewed in a vertical direction. The upper and lower elastic members 11A, 11B are spaced from each other by the maximum distance midway between the side edges 4, 5. Each of the first and second elastic members 10, 11 arranged in this manner may have a desired elasticity and elongation percentage and the individual elastic elements of the elastic members may be arranged parallel to each other in suitably spaced condition. Alternatively, the respective elastic members may have their elongation percentages varying transversely of the front body 2 and/or the rear body 3.

The front and rear bodies 2, 3 are joined by heating the thermoplastic synthetic fibers contained in the nonwoven fabric at bonding spots 20 intermittently arranged in a vertical direction along the respective side edges 4, 5, 6, 7. The front and rear bodies 2, 3 may be integrated by means of adhesive instead of the heating.

The belly protector 1 constructed as described above is intended to be used so that the transversely middle area of the front body 2 at which the upper and lower elastic members 11A, 11B are spaced from each other by the maximum distance lies on the prominence of the wearer's belly. A direct pressure exerted on the prominence can be thereby alleviated or avoided. Alternatively, the second elastic member 11 may comprise, in addition to the upper and lower elastic members 11A, 11B, other rectilinear elastic members extending parallel to the first elastic member 10. For the rear body 3, the elasticity of the upper and lower elastic members arranged on the rear body 3 may be selected to be different from those arranged on the front body 2 or a layout thereof may be selected to be different from the layout thereof of the front body 2 and thereby these elastic members may be eliminated partial or entirely.

Figure 2:
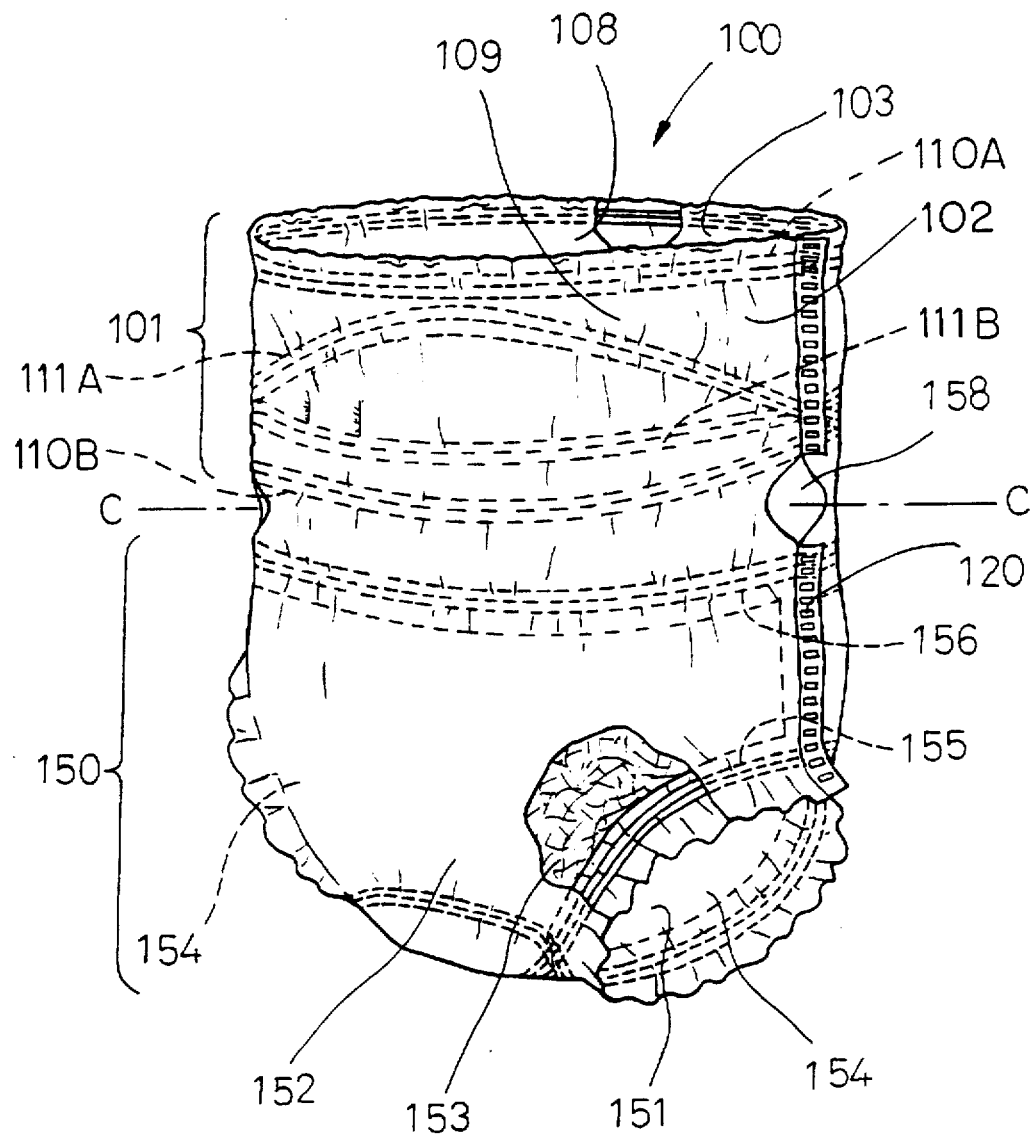
FIG. 2 is a perspective view showing another disposable undergarment comprising a belly protector and pants as partially broken away.

Referring to FIG. 2, there is illustrated another embodiment of the invention, which is a belly protector 100 integrated with a disposable diaper of pants type or a disposable training pants (both referred to hereinafter simply as pants).

The belly protector 100 comprises a belly protector section 101 and a pants section 150 formed of a continuous, non-woven fabric divided by an imaginary boundary line C—C. The belly protector section 101 defined above the line C—C has substantially the same configuration as the belly protector 1 illustrated in FIG. 1. The pants section 150 defined below the line C—C has substantially the same configuration as those disclosed in Japanese Laid-Open Patent Application Nos. Hei3-33201 and Hei3-82467, which are incorporated herein by reference.

The pants section 150 comprises a liquid-permeable topsheet 151, a liquid-impermeable backsheet 152 and a liquid-absorbent core 153 disposed between these sheets 151, 152 and has a pair of leg-openings 154 defined at transversely opposite sides of the pants section 150. Around these leg-openings 154 and a portion corresponding to a waist-opening there are provided elastic members 155 and an elastic member 156, respectively, which are secured in an elastically contractible condition to one or both of the top- and backsheets 151, 152 on its or their inner surface(s). Transversely opposite edges of the pants section 150 are provided with joining spots 120 formed in the same manner as in the case of the belly protector 1. The top- and backsheets 151, 152 extend upward beyond the line C—C so as to form respective inner and outer sheets 108, 109 defining the front and rear bodies 102, 103 of the belly protector section 101. Adjacent the line C—C dividing the belly protector section 101 and the pants section 150, the core 153 is not present. The transversely opposite edges between these sections 101, 150 may be formed, adjacent the line C—C, with cutouts; 158, if desired, to improve air-permeability of the belly protector 100 and thereby to avoid a stuffiness due to wearing of the diaper. It is possible to eliminate any one of the elastic members 111B on the belly protector section 101 and the elastic member 156 of the waist openings of the pants section 150. It is also possible to make the boundary portion between the sections 101, 150 water-repellent or water-proof in order to prevent the discharged body fluids from spreading into the belly protector section 101.

The inventive belly protector 100 integrated with the pants in this unique manner can be put on a baby without being bulky around the waist, which is usually inevitable when a separate diaper and belly protector are put on a baby, allowing for free movement of the baby's body. With the inventive belly protector 100, in addition, a direct pressure exerted on the prominence of a potbelly characterizing the babies can be avoided. It should be understood that the pants section 150 may be replaced by the conventional training pants.

The undergarment, particularly the belly protector of the invention allows a direct pressure exerted on the prominence of the wearer's belly to be alleviated or avoided when it is worn, because the front body thereof is provided along its upper and lower openings with the first elastic members and between these first elastic members with a pair of the second elastic members only curved convexly toward the upper and lower openings, respectively, so that the area of the front body at which this pair of second elastic members is spaced from each other lies on the prominence of the wearer's belly. In this manner, feelings associated with the wearing of the belly protector can be improved.

What is claimed is:

1. A disposable undergarment comprising a belly protector, said belly protector comprising:

a front body and a rear body joined together along transversely opposite side edges thereof so as to form a tubular configuration having upper and lower openings; a pair of first elastic members secured in an elastically contractible condition along said upper and lower openings, respectively; a pair of second elastic members secured in an elastically contractible condition to at least said front body between said pair of first elastic members to extend between the transversely opposite side edges of said front body with a transversely symmetric arrangement and only curved convexly toward said upper and lower openings, respectively; and one of said pair of second elastic members extending in close proximity to said lower opening.

2. A disposable undergarment comprising a belly protector and pants;

said belly protector comprising: a front body and a rear body joined together along transversely opposite side edges thereof so as to form a tubular configuration having upper and lower openings; a pair of first elastic members secured in an elastically contractible condition along said upper and lower openings; and a pair of second elastic members secured in an elastically contractible condition to at least said front body between said pair of first elastic members so as to extend between the transversely opposite side edges of said front body with a transversely symmetric arrangement and to only curve convexly toward said upper and lower openings, respectively; and said pants comprising: a front body and a rear body joined together along transversely opposite side edges thereof so as to define a waist-opening and a pair of leg-openings; and said waist-opening of said pants being seamlessly connected to said lower opening of said belly protector.

3. A disposable undergarment according to claim 2, wherein said belly protector and said pants are formed of a continuous common nonwoven fabric.

4. A disposable undergarment according to claim 2, wherein a boundary area between said belly protector and pants is formed at transversely opposite sides thereof with cutouts for air-permeability.

5. A disposable undergarment according to claim 2, wherein each said front body and said rear body of said pants comprise a liquid-permeable topsheet, a backsheet and a liquid-absorbent core disposed therebetween.

\* \* \* \* \*